United States Patent [19]

Kuzmak et al.

[11] Patent Number: 4,696,288
[45] Date of Patent: Sep. 29, 1987

[54] CALIBRATING APPARATUS AND METHOD OF USING SAME FOR GASTRIC BANDING SURGERY

[76] Inventors: Lubomyr I. Kuzmak, 657 Irvington Ave., Newark, N.J. 07106; Robert E. Hoyt, 326 El Gaucho Rd., Santa Barbara, Calif. 93111

[21] Appl. No.: 766,091

[22] Filed: Aug. 14, 1985

[51] Int. Cl.$^4$ ............................................. A61B 19/00
[52] U.S. Cl. ..................................... 128/1 R; 128/780
[58] Field of Search ............... 128/1 R, 774, 775, 778, 128/780, 748, 673, 675, 344, 780, 348.1, DIG. 25; 604/97

[56] References Cited

U.S. PATENT DOCUMENTS

| | | | |
|---|---|---|---|
| 3,661,148 | 5/1972 | Kolin | 128/774 |
| 4,402,327 | 9/1983 | Lambert et al. | 128/774 |
| 4,502,490 | 3/1985 | Evans et al. | 128/780 |
| 4,543,965 | 10/1985 | Pack et al. | 128/774 |

OTHER PUBLICATIONS

Solhaug, "Gastric Banding, A New Method in the Treatment of Morbid Obesity", Current Surgery, pp. 424-428, (Nov.-Dec. 1983).

*Primary Examiner*—Dalton L. Truluck
*Assistant Examiner*—Mario Costantino
*Attorney, Agent, or Firm*—Daniel J. Meaney, Jr.

[57] ABSTRACT

A calibrating apparatus adapted to be inserted into and proceeded within the stomach of human body which includes a single-lumen tubing terminating in a proximal portion and a distal tip each of which have an orifice and wherein the single-lumen tubing has a first opening extending therethrough which is located at a selected distance from the proximal portion and a second opening which extends therethrough and which is located a predetermined distance from the distal tip, an elongated, thin-walled sensor having a circular-cross section and a cavity within the interior thereof and which is operatively coupled in a sealing relationship to the distal tip wherein the thin-walled sensor is capable of having its cross-sectional diameter varied in response to a force applied to the exterior of the sensor to vary the pressure of a fluid within the cavity, a balloon surrounding the exterior of said single-lumen tubing at the preselected location which encloses the second opening and an elongated tubing member which extends through the single-lumen tubing, through the first opening and into communication with the second opening is shown. A method for performing a gastric banding operation on the stomach of a human being utilizing the calibrating apparatus is also shown.

8 Claims, 23 Drawing Figures

CALIBRATING APPARATUS AND METHOD OF USING SAME FOR GASTRIC BANDING SURGERY

BACKGROUND OF THE INVENTION

1. Field of the Invention

This invention relates generally to the field of gastroplasty, which is as a special surgical procedure for controlling obesity, and more particularly relates to an improved special surgical procedure which utilizes a calibrating apparatus, which adapted to be inserted and proceeded within the stomach, in conjunction with a gastric banding surgical procedure to form the stomach into an upper cavity and lower cavity with a small passageway having a predetermined diameter communicating therebetween.

2. Description of the Prior Art

It is known in the art, since the early 1960's, to utilize surgical procedures on the stomach as a means for treating obesity. In performing such surgery, invasive surgery in the form of making an incision into the stomach, use of staples or use of suturing procedures was required in order to control the size and volume of the stomach cavity. By controlling the size or volume of the stomach cavity, the food receiving cavity was reduced in size to limit the amount of food which a patient could eat before feeling full, which resulted in weight reduction.

In 1980, at the Ullevaal in Oslo, Norway and in Houston, Tex., a special surgical procedure known as gastric banding was developed as the simplest and least invasive operation for morbid obesity. The gastric banding operation utilized a dacron vascular graft which is placed around the upper part of the stomach and the dacron vascular graft was used in place of stapling. The gastric banding provided an improvement over the known surgical techniques because it was the least invasive operation for morbid obesity because the stomach is not crushed, cut or penetrated by staples or sutures in performing the operation.

As a result of the known surgical procedures, undesirable side effects were experienced in terms of unwanted tissue reaction and adhesions developing at the surgical site.

It was also known in the art to perform a vertical banding gastroplasty wherein the stomach is divided into an upper and lower pouch by forming a passageway in the side of the stomach. In such surgery, it was difficult to control the size of the passageway between the upper and lower pouches. In order to control the size of the passageway cavity, a hand held probe was inserted into the stomach and the stomach was sutured or stapled around the probe in order to obtain a desired diameter for the passageway. The hand held probe was then removed completing the surgery.

SUMMARY OF THE INVENTION

The present invention provides a novel, unique and improved calibrating apparatus which was adapted to be inserted into a proceeded within the stomach of a human body. In the preferred embodiment, the calibrating apparatus is adapted to be utilized as part of an improved method for performing a gastric banding operation on the stomach of a human body.

The calibrating apparatus of the present invention includes a single-lumen tubing which terminates in a proximal portion at one end thereof and distal tip at the other end thereof. The proximal portion of the single-lumen tubing has a first orifice which communicates with the interior of a single-lumen tubing and which has, at a selected location from the first orifice, a first opening which extends from the interior of the single-lumen tubing to the exterior thereof. The other end of the single-lumen tubing has, at a predetermined distance from the distal tip, a second opening which extends from the interior of the single-lumen tubing to the exterior thereof. Also, the other end has a second orifice located at the distal tip which communicates with the interior of a single-lumen tubing. Operatively coupled in a sealed relationship to the distal tip is an elongated, thin-walled sensor having a circular cross-section and means defining a cavity within the interior thereof which terminates an aperture at one end thereof and the other end thereof closed. The aperture of the sensor communicates with the second orifice of the single-lumen tubing. The the thin-walled sensor is capable of having its cross-sectional diameter varied in response to a variable force being applied to the exterior of the sensor. The sensor is responsive to a variable force by varying the pressure of a fluid in the cavity defined within the thin-walled sensor. A balloon is operatively coupled to and surrounds the exterior of the single-lumen tubing at a preselected location near the distal tip. The balloon is positioned to enclose and to have the second opening communicating within the interior of the ballooon. An elongated tubing member extends from a location exterior to the single-lumen tubing, through the first opening located adjacent to the first orifice with the exterior of the tubing being in sealing engagement with the first opening and into communication with second opening and the interior of the balloon enclosing the second opening. A means operatively coupled to the first orifice is provided which adapted to maintain a fluid under pressure within the interior of a single-lumen tubing and in the cavity of the thin walled sensor. The fluid contained by the fluid maintaining means is capable of having its pressure varied in response to a variable force being applied to the exterior of the sensor.

The calibrating apparatus of the present invention is adapted for use in a method for performing a gastric banding operation on the stomach of a human body. The method comprises the steps of inserting the calibrating apparatus into the opening of human body and proceeding the calibrating apparatus into the interior of the stomach; inflating the balloon while the calibrating apparatus is within the stomach by passing a fluid under pressure through the elongated tubing to expand the balloon to a selected expanded dimension and retrograding the inflated balloon against the stomach opening; constricting the stomach located immediately below the expanded balloon by applying an adjustable gastric band around the periphery of the stomach and urging the interior of the stomach into engagement with and around the exterior of the sensor; tightening the adjustable gastric band around the periphery of the stomach until a predetermined pressure is detected as being applied to the exterior of the sensor to form a passageway between the inner walls of the stomach wherein the passageway has a diameter which is substantially equal to the cross-sectional diameter of the sensor at a predetermined applied pressure to establish an upper cavity having a volume which substantially equal to the selected expanded dimension of the a balloon and a lower cavity which communicates with the first cavity through the passageway having the predetermined crosssectional area; suturing together the side walls of the stomach forming the upper and lower cavities and enclosing the adjustable gastric band to define an annular-shaped opening around the adjustable gastric band and withdrawing the fluid from the interior of the balloon, collapsing the same, and retrograding the calibrating apparatus through the opening of the first cavity and out of the human body.

The calibrating apparatus and the method of using the same represents a significant improvement over the known the prior art method of gastric banding wherein it is difficult to control the size of the passageway extending from the upper cavity to the lower cavity of the stomach. The calibrating apparatus of the present invention enables a surgeon in performing the gastric banding operation to precisely set the diameter of the passageway extending from the upper cavity to the lower cavity of the stomach.

In known art procedures, a surgical probe was required to be inserted into the stomach and the surgeon had to manually feel the location of the probe and then sutured the stomach around the probe to establish the diameter of the passageway between the upper and lower cavity.

One disadvantage of the known prior art surgical procedures was that the diameter of the passageway between stomach cavities could not be precisely controlled. In such instance, the diameter of the passageway between the upper cavity and the lower cavity may be too big or too small. The result is that the stomach does not properly receive and pass food which may cause an adverse reaction to the patient. The present invention overcomes the disadvantage of the prior art by providing a calibrating apparatus which is capable of presently controlling the diameter of the passageway at a predetermined diameter. In the preferred embodiment, the diameter of the passageway is approximately 13 millimeters, a little small than a size of a dime. A passageway having a diameter of this size operates to precisely limit the amount of food eaten at one particular time and the opening slows down the passage of food from the upper cavity to the lower cavity. If the size of the passageway is too large or too small, the desired effect on the patient cannot be achieved.

The calibrating apparatus utilizes a pneumatic sensing system which monitors the pressure of sensor. The sensor is responsive to pressure being applied to the exterior thereof by an adjustable gastric band during constriction of the stomach. A direct relationship exists between the pressure being exerted on the exterior of the sensor and the size of the passageway. By sensing and monitoring the pressure being applied to the calibration apparatus, the surgeon can be provided with visual indications during the surgical procedure as to whether the band is too loose or too tight. When the band is set at exactly the right pressure, a visual indication is provided to the surgeon indicating that the desired pressure has been obtained which means that the cross-sectional diameter of the passageway is at the predetermined dimension desired by the surgeon.

One advantage of the present invention is that the calibrating apparatus can be used to precisely establish the diameter of an opening. In the preferred embodiment, the calibrating apparatus is responsive to pressure applied to the exterior surface of a sensor by an adjustable gastric band during surgery. The pressure in the sensor is capable of being monitored by a monitoring system which indicates when a predetermined pressure has been obtained. When the predetermined pressure is obtained, the passageway diameter is at a predetermined cross-sectional dimension which is equal to that of the sensor of the calibrating apparatus. The surgeon can then selectively vary the diameter of the sensor to establish the passageway diameter at a different selected diameter.

Another advantage of the present invention is that the calibrating apparatus is adapted to be utilized with a pneumatic system wherein pressure is maintained within the interior of the single-lumen tubing and cavity of the sensor and wherein the change in pressure is transmitted through a closed fluid channel. The closed fluid channel is, in turn, monitored by a monitoring system which indicates changes in pressure. The changes in pressure are converted to visual indications to represents when the adjustable band is to loose, too tight, or is at the right diameter.

Another advantage of the present invention is that the calibrating apparatus includes a toroidal shaped balloon which can be expanded to a selected expanded dimension to establish the volume or capacity of the upper cavity to be formed within the stomach.

Another advantage of the present invention is that the stomach in a human body is generally uneven with a smaller left side and larger right side. The inflatable balloon has the ability to shift to accommodate the different sizes of stomachs and also is able to establish a desired volume in the upper cavity formed within a stomach.

Another advantage of the calibrating apparatus of the present invention is that the calibrating apparatus can be passed through the esophagus and is of such a size that it does not damage, irritate or otherwise injure the esophagus.

Another advantage of the present invention is that by use of the pneumatic closed fluid channel and the use of a temperature stabilization technology, variations in sensor pressure in the order of 0.02 psi can be accurately detected.

Another advantage of the present invention is that a dacron reinforced silicone gastric band can be utilized in lieu of a vascular graft. The dacron reinforced silicone gastric band has the advantage of eliminating unwanted tissue reaction and adhesions that occurs when vascular grafts are used. A dacron mesh is incorporated into the gastric band to prevent the gastric band from stretching after it has been adjusted to the desired size.

Another advantage of the present invention is that the adjustable gastric band may be fabricated with an interior section which may be inflated or deflated through a subcutaneous injection site slightly below the surface of the skin. This permits a surgeon to adjust the gastric band after surgery to control the size of the restriction.

Another advantage of the present invention is that, in the preferred embodiment, by controlling the the diameter of the passageway to about 13 millimeters, the small capacity of the upper cavity limits the amount of food eaten at one particular time and the passageway having a predetermined diameter controls the passage of food into the lower cavity of the stomach. The preferred range of passageway diameters is about 10 millimeters to about 13 millimeters.

Another advantage of the present invention is that monitoring system utilizes different colored lights or a series of sequentially operated lights which are capable of being illuminated to indicate the tightness of the band. If the band too loose, the opening will be too large and the patient will eat too much. If the band is placed too tight, the opening will be too small which may result in excess vomiting. By utilizing the calibrating apparatus of the present invention the size of the opening established by the adjustable band is controllable and predictable.

Another advantage of the present invention is the calibrating apparatus without the balloon and its associated elongated tubing member can be utilized in for measuring sizes of openings for a number of applications including the known vertical banding gastroplasty.

BRIEF DESCRIPTION OF THE DRAWINGS

These and other objects and advantages of the invention, together with its various features and advantages, can be more easily understood from the following more detailed description of the preferred embodiment taken in conjunction with the accompanying drawing in which:

FIGS. 14(a), 14(b), 14(c) and 14(d) illustrate the steps for utilizing the calibrating apparatus of the present invention in a method for performing a gastric banding operation on the stomach of a human body;

DESCRIPTION OF THE PREFERRED EMBODIMENT

Figure 1:
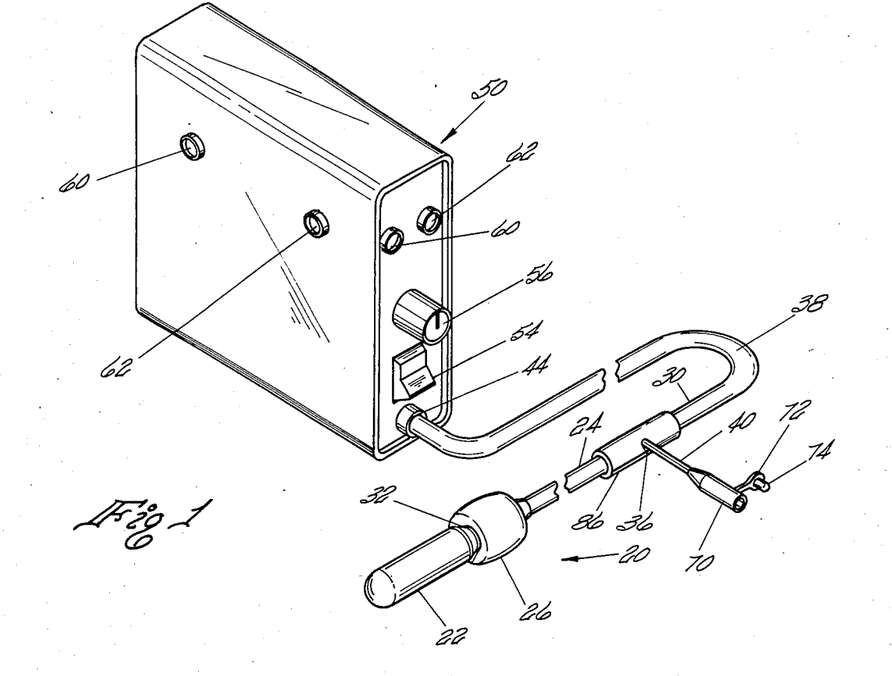
FIG. 1 is a perspective view of a monitoring apparatus having a calibrating apparatus of the preferred embodiment operatively attached thereto through a pneumatic tubing system.

FIG. 1 illustrates a preferred embodiment of a calibrating apparatus utilizing the teachings of the present invention. The calibrating apparatus 20 includes a single-lumen tubing 24 which is operatively coupled to an elongated, thin-walled sensor 22. The elongated, thin-walled sensor is in sealing engagement to the single-lumen tubing 24. A balloon 26 is operatively coupled to and surrounds the exterior of the single-lumen tubing 24. The balloon 26 is located at a preselected location near the distal tip shown generally as 32. The single-lumen tubing has a proximal end shown generally as 30 which has a first opening 36 which extends from the exterior of the single-lumen tubing 24 into the interior thereof. An elongated tubing member 40 extends from a location exterior to the single-lumen tubing 24, through the first opening 36 and into communication with a second opening and interior of the balloon 26 which is illustrated in greater detail in FIG. 3. The single-lumen tubing 24 is operatively connected through a closed fluid channel, which in the preferred embodiment is a pneumatic tubing 38. Depending on the construction of the device, the single-lumen tubing can have the proximal end thereof formed into the pneumatic tubing 38. In the alternative, the pneumatic tubing 38 could be a separate flexible tubing which is operatively coupled to the first orifice located at the proximal portion of the single-lumen tubing 24. The pneumatic tubing 38 may be operatively connected through a transducer, illustrated in FIG. 20, and into an input 44 of the monitoring apparatus shown generally as 50. The monitoring apparatus 50 includes an on and off switch 54, a sensitivity adjustment means 56, illumination lights shown both on the front panel and side panel which are identified as lights 60 and 62, respectively.

An elongated tubing member 40 is operatively coupled to the single-lumen tubing 24. In the preferred embodiment, the elongated tubing member 40 terminates in a valve 70 having a closure member 72. Closure member 72 is adapted to be rotated such that its protruding tab 74 can be inserted into the interior of the valve 70. When the protruding tab 74 is inserted into the valve 70, the valve is in a closed position and occludes the fluid within the elongated tubing 40 and balloon 26. The valve 70, when in the opened position as illustrated in FIG. 1, is adapted to receive and pass a fluid therethrough into the elongated tubing member 40 through a second opening and into an expanding engagement with the balloon 26. Thereupon, the closure member 72 can be rotated such that protruding tab 74 thereof is inserted into the opening of valve 70 to occlude the elongated tubing member 40, to maintain the balloon 26 at a selected expanded dimension. In use, a syringe 80 is inserted into valve 70 and is used to apply a controlled volume of fluid into the balloon to expand the same to a selected expansion dimension.

Figure 2:
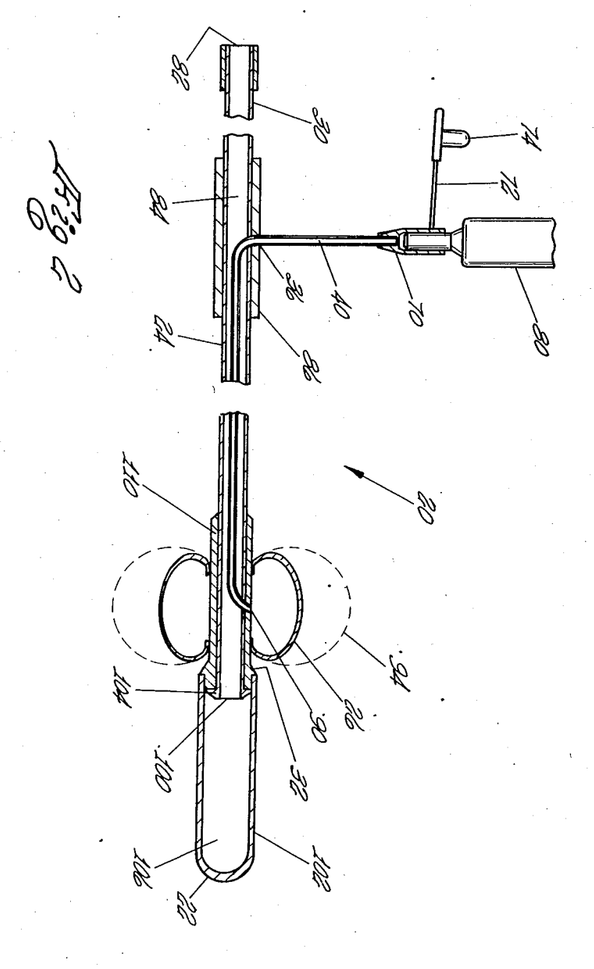
FIG. 2 is a partial pictorial representation in cross-section of the calibrating apparatus.

FIG. 2 illustrates in greater detail the structure of the calibrating apparatus 20 which is adapted to be inserted into and proceeded within the stomach of a human body. The calibrating apparatus 20 includes the single-lumen tubing 24 which terminates in a proximal portion 30 at one end thereof and a distal tip 32 at the other end thereof. The proximal portion 30 has a first orifice 82 which communicates with the interior 84 of the single-lumen tubing 24. The proximal portion 30 has, at a selected location from the first orifice 82, a first opening 36 which extends from the interior 84 of the single-lumen tubing 24 to the exterior thereof. The other end thereof has at a predetermined distance from the distal tip 32 a second opening 90 which extends from the interior 84 the single-lumen tubing to exterior thereof. Also, the distal tip 32 includes a second orifice 100 which communicates with the interior 84 of the single-lumen tubing.

The elongated, thin-walled sensor 22 has a circular cross-section and includes a thin wall 102 which defines a cavity 106 within the interior thereof. The cavity 106 terminates an aperture communicating therewith at one end thereof and which has its other end thereof closed. The thin-walled sensor 22 is operatively coupled in a sealed relationship by a coaxial sealing member 110 which communication with a lip 104 formed at the second orifice 100 at the distal tip 32. The coaxial conical shaped sealing member 110 is attached to the balloon 26 to ensure that the edges of the balloon 26 are in a sealing engagement with and are positioned around the exterior of a single-lumen tubing 24. The thin-walled sensor 22 is capable of having of its cross-sectional diameter varied in response to a variable force being applied to the exterior of the sensor. The sensor 22 is responsive to the variable force by varying the pressure of a fluid placed into the cavity 106.

The balloon 26 is operatively coupled to and surrounds the exterior of the single-lumen tubing 24 at a preselected location near the distal tip end 32. The balloon 26 is positioned to enclose and to have the second opening 90 in communication with the interior of the balloon 26. The balloon 26 can be inflated from its collapsed or deflated position into a selected expanded dimension, illustrated by dash line 94, having a controlled volume.

The elongated tubing member 40 extends from the location exterior to the single-lumen tubing 24, through the first opening 36 located adjacent to the first orifice 82. The exterior of the tubing member 40 is in sealing engagement with the first opening 36 to ensure that the fluid contained within cavity 84 would not leak out. The elongated tubing 40 then passes through the interior 84 of the single-lumen tubing 24 and into communication with the second opening 90 and the interior of the balloon 26 which encloses the second opening.

The single-lumen tubing 24 can then be attached to or communicate with a second pneumatic tubing 38 as illustrated in FIG. 1. In the alternative, the single-lumen tubing 24 itself can be extended into communication with the inlet 44 located on the monitoring apparatus 50.

Figure 3:
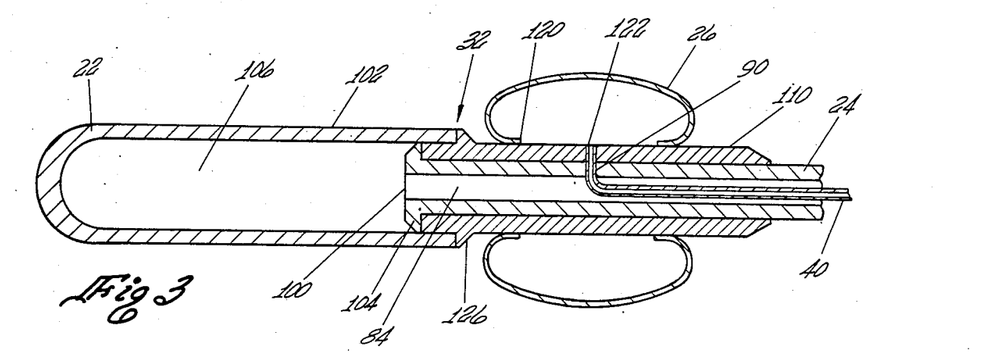
FIG. 3 is a partial cross-section showing the detail construction of the distal tip of the single-lumen tubing and the sensor operatively attached thereto in sealing engagement therewith.

FIG. 3 illustrates in greater detail the structural relationship of the various components at the distal tip 32 of the calibrating apparatus. The single-lumen tubing 24 has a coaxially aligned, conical shaped sealing member 110 formed around the periphery thereof which terminates in a ridge 126 which is located near the second orifice 100. The end of the single-lumen tubing 24 defining the second orifice 100 also includes means defining a tip 104 which is formed therearound. The lip 104 is brought into sealing engagement with the end of the sealing member 110. The end of the thin-walled 102 is positioned in sealing engagement with the lip 126. Thus, the cavity 106 is fluid tight and any fluid within the interior 106 of sensor 22 communicates through orifice 100 with the interior 84 of the single-lumen tubing 24. The coaxial, conical shaped sealing member 110 is operatively connected to the edge of the balloon 26 to form a fluid tight seal therearound. The sealing member 110 likewise has an orifice 122 which communicates with the second opening 90 extending through the wall of the singlelumen tubing 24. The pneumatic system, which includes the elongated tubing member 40, for inflating and deflating the balloon 26 is separate from the fluid pressure monitoring system associated with the interior 84 of the single-lumen tubing 24 and the cavity 106 of sensor 22.

As is readily apparent from FIG. 3, the balloon 26 can be collapsed or deflated during insertion and proceeding of the calibrating apparatus within the human body. Also, the balloon 26 is deflated during the withdrawal process. When the calibrating apparatus 20 is in position within the stomach, the balloon 26 then can be inflated to a selected expanded dimension by use of syringe 80 as illustrated in FIG. 2. The balloon 26 can be maintained at the selected expanded dimension by keeping the syringe 80 in position within the valve 70 or, in the alternative, by removing the syringe 80 from the valve 70 and utilizing the closure member 72 such that the protruding tab 74 is inserted into the cavity within the interior of valve occluding the elongated tubing member 40 to maintain the expansion of the toroidal-shaped balloon at a selected expanded dimension same.

Figure 4:
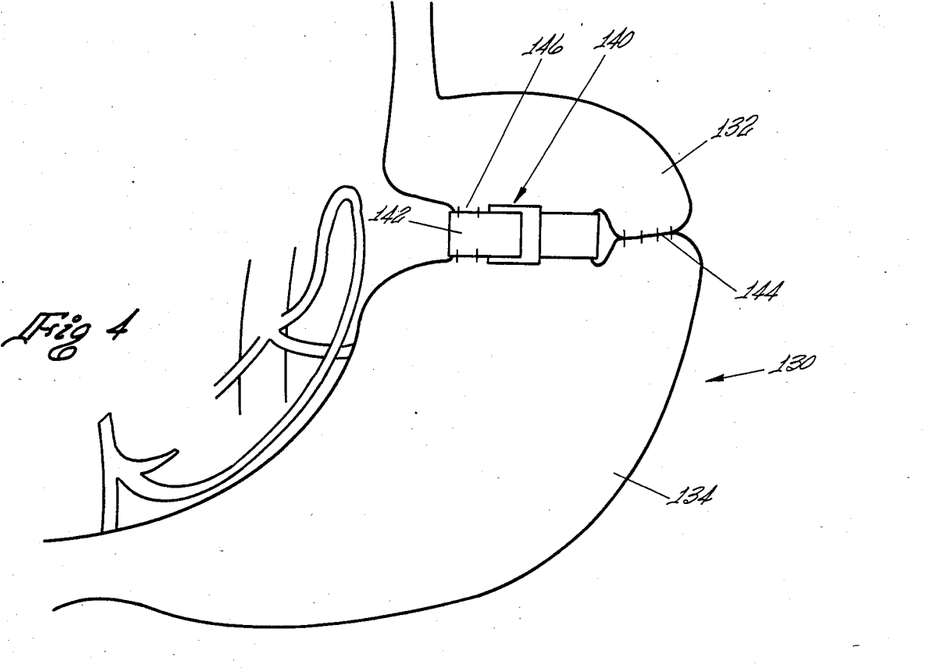
FIG. 4 is a pictorial representation of a stomach of a human body having an adjustable gastric band forming a constriction in the stomach dividing the same into upper and lower cavities.

The preferred use of the calibrating apparatus of the present invention is in a method for performing a gastric banding operation on the stomach of human body. FIG. 4 illustrates how the stomach will appear upon completion of surgery using the calibrating apparatus and method of of this invention.

FIG. 4 illustrates the desired result of the gastric banding surgery which is performed by utilizing the calibration apparatus of the present invention. Upon completion of the surgery, the stomach 130 in a human body is formed into an upper cavity 132 having a predetermined volume in the order of one (1) ounce or about 30 milliliters to about 50 milliliters capacity. The upper cavity 132 is generally referred to as a gastric pouch. The stomach 130 also has a lower cavity 134 which is operatively connected through a passageway shown generally as 140 which has been formed within the stomach by use of an adjustable gastric band 142 which forms a constriction within the stomach 130. The diameter of the passageway 140 is precisely controlled and is set at a predetermined diameter of about 13 millimeters. The adjustable gastric band 142 is sutured to the stomach, as shown by sutures 146, by the surgeon in order to ensure that the diameter of the passageway will not change and that the adjustable gastric band 142 will not migrate. The stomach walls forming the upper cavity 132 and the lower cavity 134 are sutured together by means of 3-0 silk sutures illustrated as 144.

Figure 5:
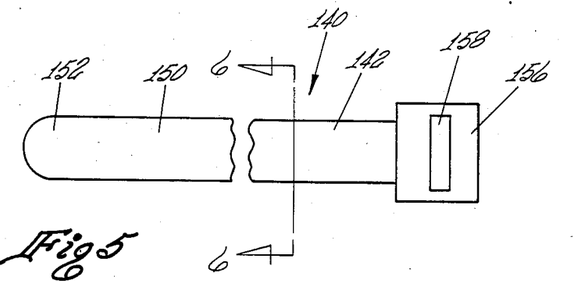
FIG. 5. is a pictorial representation of a dacron reinforced silicone adjustable gastric band to be used in practicing the invention.

FIG. 5 illustrates a preferred embodiment of the adjustable gastric band 142. One gastric band which can be utilized in practicing this invention is presently offered for sale and sold by Mentor Corporation Experimental Exemption Devices. However, it is envisioned that any one of numerous gastric bands may be used in practicing this invention. This gastric band is formed of a elongated strap member 150 which terminates with a tongue 152 at one end. The other end of the strap 150 terminates in a fastening member 156 which has the elongated slot 158 formed therein. In use, the tongue 152 of the elongated strap 150 is inserted into and is passed through the elongated slot 158 as illustrated in FIG. 4.

Figure 6:
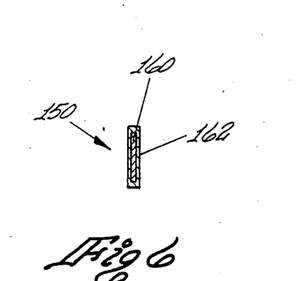
FIG. 6 is a section taken along section lines 6—6 of FIG. 5.
Figures 7, 8:
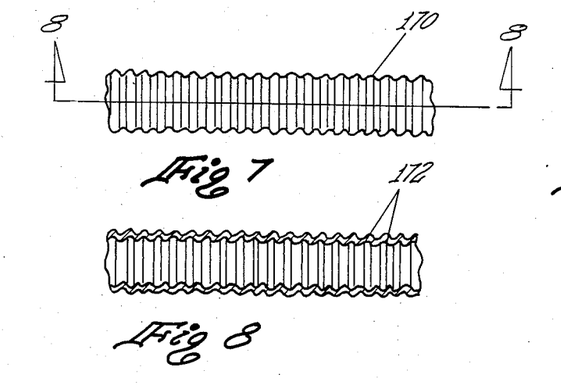
FIG. 7 is a pictorial representation of a dacron vascular graft adapted to be used as a gastric band for practicing this invention.
FIG. 8 is a cross-sectional view of the dacron vascular graft taken along section lines 8—8 of FIG. 7.

FIG. 6 illustrates the construction of the gastric band of FIG. 5. The strap 150 includes a central member 160 which is laminated or covered by an outer surface 162. The gastric banding is formed of a material which is flexible, but which does not yield or stretch during adjustment of the surgical procedure or, when the surgical procedure is completed, will retain its integrity. The gastric banding is formed of a material which compatible to the body such as silicone thereby eliminating the undesirable side effects of adhesions or unwanted tissue reaction. In the preferred embodiment, the gastric band 142 can be formed of a central member having a dacron mesh to prevent the gastric band from stretching and the exterior thereof is covered by a silicone exterior.

Figure 9:
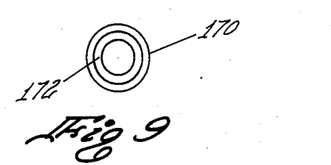
FIG. 9 is an end plan view of the dacron vascular graft adapted to be used as a gastric band.
Figure 10:
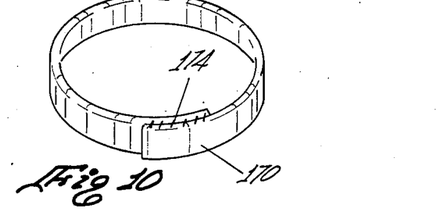
FIG. 10 is a pictorial representation of a suturing pattern used for retaining the dacron vascular graft adapted to be used as a gastric band at the predetermined diameter.

FIGS. 7, 8, 9 and 10 illustrate another banding material in the form of a dacron reinforced vascular graft 170, which can be used for the gastric band. The vascular graft material is formed with ridges and thin walls 172 therein to provide some rigidity. The vascular graft material has a circular cross-section as illustrated in FIG. 9. During surgery, the dacron vascular graft material is pulled into an annular shaped member as illustrated in FIG. 10 causing the circular shaped cross-sectioned illustrated in FIG. 9 to collapse and become flat. This causes each of the side walls of the graft material 170 to be brought into contact with each other. The annular shaped member 170 as illustrated in FIG. 10 is sutured at the ends thereof by sutures 174 to maintain the predetermined dimension thereof.

Figures 11, 12, 13, 14:
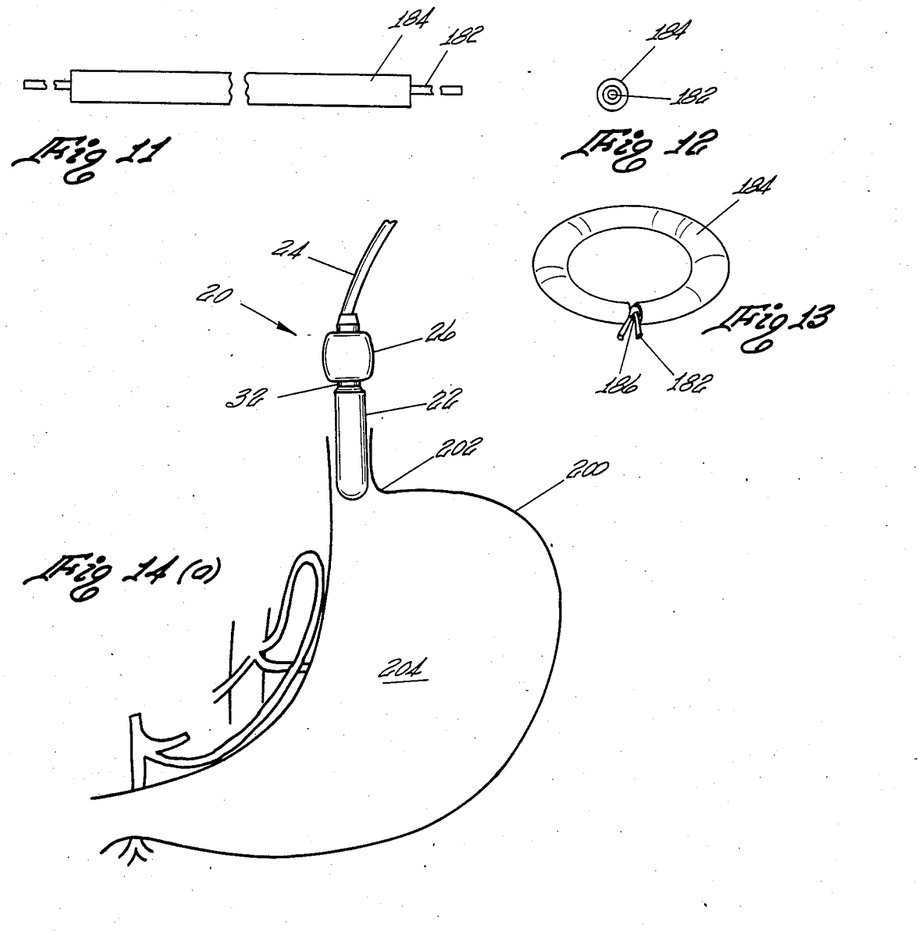
FIG. 11 is a pictorial representation of another type of gastric band having an elongated, cord-like central member having a flexible firm protective member formed therearound and wherein the elongated, cord-like central member is capable of being tied to form an opening of a predetermined dimension.
FIG. 12 is an end plan view of the gastric band of FIG. 11.
FIG. 13 is a pictorial representation of the gastric band of FIG. 11 tied into a band with a predetermined diameter.

FIGS. 11, 12 and 13 show another embodiment of a gastric band which can be utilized for practicing the invention. The gastric band in FIGS. 11, 12 and 13 includes a cord like central member 182, which may be a dacron rope mesh, which is encircled with a biologically stable material 184, such as silicone, extending around the periphery thereof. The cord like central member 182 extends sufficiently beyond the coaxial member 184 so as to form ends which can be tied by a surgeon during surgery. FIG. 13 illustrates the gastric band with the ends 182 thereof tied into a knot 186 during surgery to estbalish the predetermined dimension.

Alternatively, the adjustable gastric band may be fabricated to have an inflatable central section wherein the band may be inflated or deflated through a subcutaneous injection site slightly below the surface of the skin to adjust the same after surgery is completed. This provides the surgeon with a means of adjusting the size of the restriction after surgery.

FIG. 14(*a*) through FIG. 14(*d*) illustrate certain of the steps required for practicing the method of the present invention. The method illustrated by the steps of FIG. 14(*a*) through FIG. 14(*d*) relate to a method for preparing a gastric banding operation on the stomach of a human body utilizing the calibration apparatus described as the preferred embodiment hereinabove. As illustrated in FIG. 14 (*a*), the calibrating apparatus 20 having the single-lumen tubing 24, the balloon 26 and the sensor 22 operatively attached at the distal end 32 of the single-lumen tubing 24 is inserted into the stomach 200 of a human body through opening 202. The calibrating apparatus 20 is proceeded into the interior 204 of the stomach 200. The calibrating apparatus is proceeded sufficiently far into the interior 204 of stomach 200 so that the balloon 26 is passed through and beyond the opening 202.

Figures 14B, 14C:
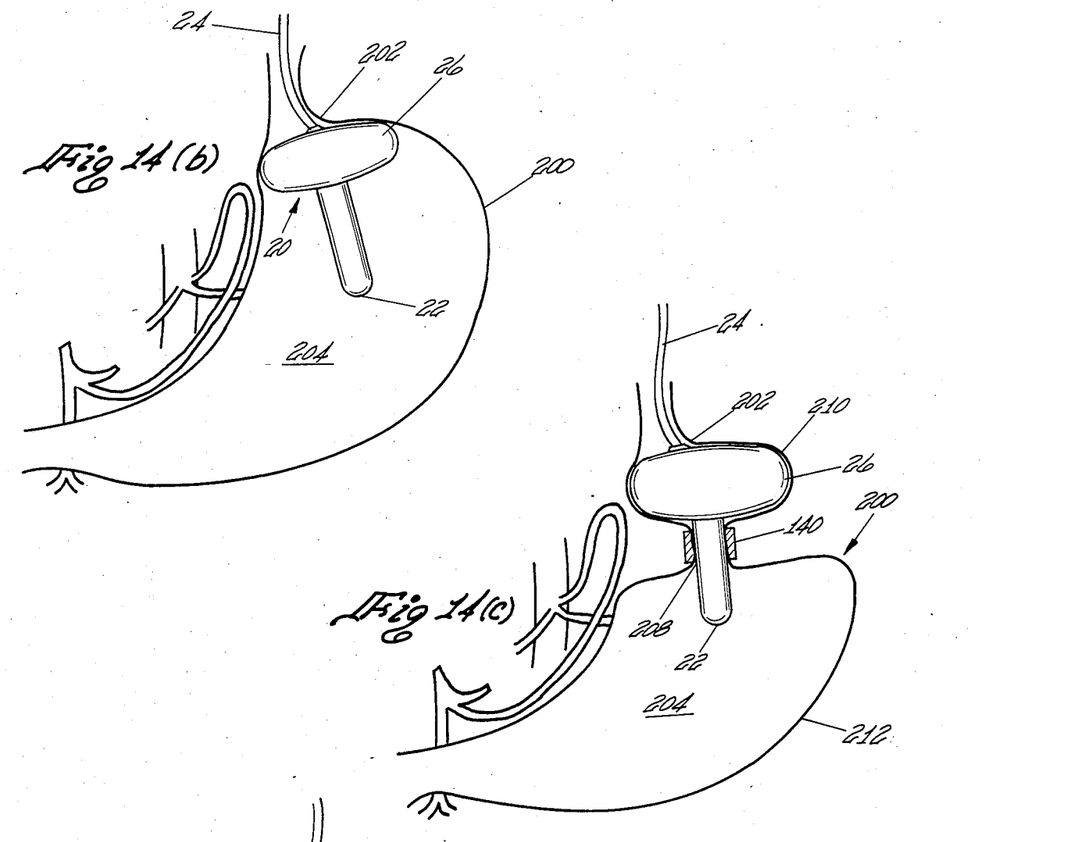

FIG. 14(*b*) shows the next step of inflating the balloon 26 while the calibrating apparatus 20 is within the interior 204 of the stomach 200. The balloon 26 is inflated by passing a fluid under pressure through the elongated tubing located within the single-lumen tubing 24 to expand the balloon to a selected expanded dimension as explained in connection with FIG. 2. The expanded or inflated balloon 26 is then retrograded or pulled against the stomach opening 202.

FIG. 14(*c*) illustrates the next step of constricting the stomach 200 located immediately below the expanded balloon 26 by applying an adjustable gastric band 140 around the periphery of the stomach and urging the interior of the stomach 200 into engagement with and around the exterior of the sensor 22. Thereupon, the step of tightening the adjustable gastric band 14 around the periphery of the stomach 200 is performed until a predetermined pressure is detected as being applied to the sensor through the monitor apparatus illustrated in FIG. 1. When the predetermined pressure is detected, the surgeon then sutures the band to itself to set the opening size and then removes the buckle. As the adjustable gastric band 140 is tightened, a passageway 208 if formed between the inner walls of the stomach 200. The passageway 208 has a diameter which is substantially equal to the cross-sectional diameter of the sensor 22 at a predetermined applied pressure developed by the tightness of the adjustable gastric band 140. However, the surgeon can then selectively vary the diameter of the sensor to establish the passageway diameter at a different selected diameter. The adjustable gastric band 140 establishes an upper cavity 210 having a volume which is substantially equal to the selected expanded dimension of the balloon 26. The lower cavity 212 communicates with the first cavity 210 through the passageway 208 having a predetermined cross-sectional diameter. The exterior dimension of the sensor 22 is in the order of 12 millimeters to 13 millimeters and the cross-sectional diameter thereof is varied by the of pressure applied by the adjustable gastric band 140 thereagainst. The variance of the cross-sectional diameter of the sensor 22 changes the pressure applied to the fluid within the cavity of the sensor 22 which can be easily monitored. Pressure changes in the order 0.02 psi can be measured and converted into precise changes in geometrical dimensions. As the surgeon adjusts the gastric band 140, the monitoring apparatus includes a plurality of visual lighting members which indicate the band is too loose, too tight or is at the right geometrical dimension. The monitoring apparatus is responsive to the pressure being applied against the exterior walls of the sensor 22 to advise the surgeon if the applied pressure reaches a predetermined pressure which, in turn, represents that the desired predetermined cross-sectional diameter of the passageway 208 has been achieved. In the preferred embodiment, the passageway 208 has a diameter dimension of approximately 13 millimeters.

Figure 14D:
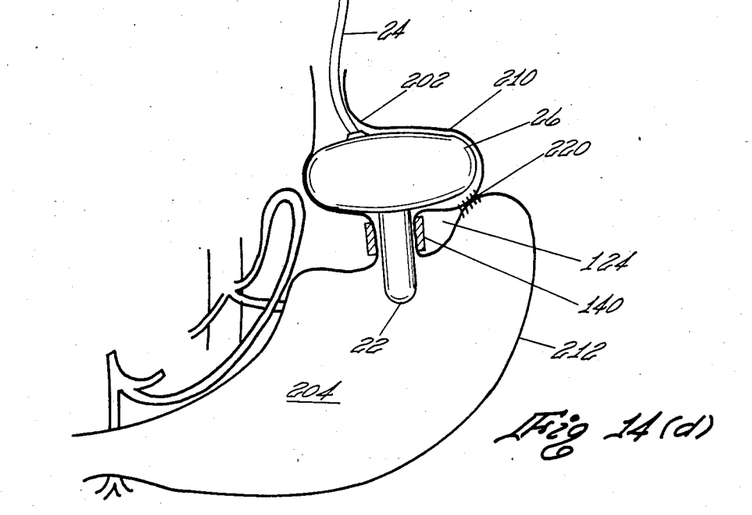

FIG. 14(d) represents the next step of suturing together the sidewalls of the stomach 200 which is formed into the upper cavity 210 and the lower cavity 212 so as to enclose the gastric band 140 when the stomach sidewalls are sutured. As illustrated by sutures 220, an annular-shaped opening 124 is formed around the gastric band 140.

Thereafter, the next step is to withdraw the fluid from the balloon 26 collapsing the same so that the calibrating apparatus, which would then be similar in appearance as to that illustrated in FIG. 14(a), is retrograded through opening 200, which is the opening into the first cavity 210, and out of the human body.

Figure 15:
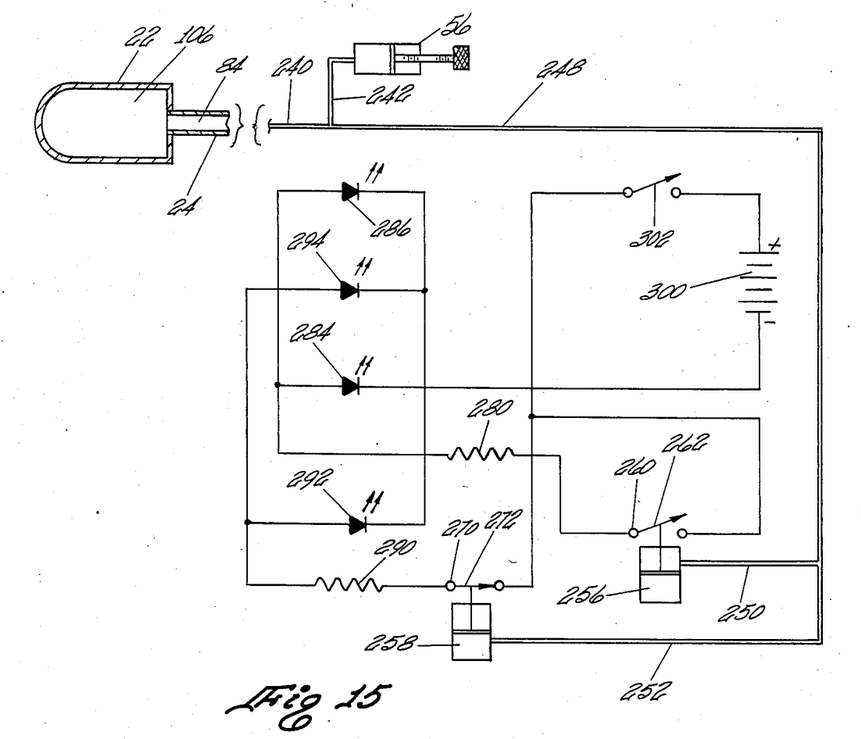
FIG. 15 is a pictorial representation including a schematic diagram showing a monitoring system which is adapted for producing visual indications to a surgeon as to the tightness of the gastric band.

FIG. 15 illustrates the basic components of the monitoring system. The sensor 22 is illustrated pictorially to have a cavity 106 which communicates with the single-lumen tubing 24 having its interior 84. The fluid contained within the interior 84 of the single-lumen tubing 24 and within the cavity 106 of sensor 22 is essentially contained in a closed fluid system. A transducer illustrated in greater detail in FIG. 20, may be used to transmit variations in pressure from the closed fluid system within the calibrating apparatus 20 through a closed fluid channel 240 into the monitoring apparatus. The closed fluid channel 240 has a branch 242 which terminates in the sensitivity adjustment means 56 and a branch 248 which continues within the interior of the monitoring apparatus. The closed fluid channel 248 is bifurcated into bifurcations 250 and 252. Bifurcations 250 and 252 terminate at pressure responsive switching means 256 and 258, respectively. The pressure responsive switching means 256 and 258 are responsive to the pressure level within its associated closed fluid bifurcated channel to operate a single pole switching means. Pressure responsive switching means 252 actuates switch 260 to switch a single pole member 262 between an open and closed position. In it normal operation, pole member 262 is in a normally open position.

In a similar manner, pressure responsive switching means 258 is responsive to the pressure in its associated bifurcated enclosed fluid channel to actuate switch 270 having a single pole member 272. In a normal operation, switch 270 is in a normally closed position.

Single pole member 262 controls light emitting diodes 284 and 286 by applying a voltage there across through a voltage dropping resistor 280 when the single pole member 262 is closed. When the single pole member is in the open position, no voltage is applied to the light emitting diodes 284 and 286.

Pressure responsive switching means 250 controls single pole member 272 to apply a voltage through voltage dropping resistor 290 to light emitting diodes 292 and 294. When the single pole member 272 is closed, the voltage is applied to the light emitting diodes 292 and 294. A voltage is applied across the light emitting diode matrix from a voltage source, such as a battery 300, which is operatively connected to the light emitting diodes through on and off switch 302.

In the switching scheme as illustrated in FIG. 15, as the surgeon begins to adjust the gastric band, the pressure within the bifurcated closed fluid channels 250 and 252 is sufficiently low such that normally closed switch 272 remains closed causing light emitting diodes 292 and 294 to remain lit showing that the gastric band needs to be tightened. As the pressure increases due to the adjustable gastric band becoming tight around the sensor 22, the fluid within the closed fluid channel 250 will actuate pressure responsive switching means 256 causing the normally open contact 262 to be closed. The pole member 262 energizes light emitting diodes 284 and 286. At that juncture, both sets of light emitting diodes are illuminated indicating that the gastric band force against the sensor is producing a predetermined pressure on the sensor which represents passageway opening is at a predetermined cross-sectional diameter. If the surgeon continues to tighten the adjustable gastric band, the pressure will increase which will cause the pressure responsive switching means 298 to open normally closed pole member 272 which would extinguish light emitting diodes 292 and 294. This would indicate on the monitoring apparatus that the gastric band needs to be loosened. When the surgeon loosens the gastric band, the pressure is reduced on the sensor and, both sets of light emitting diodes would then be illuminated advising the surgeon that the appropriate pressure and predetermined dimension has been obtained.

Figure 16:
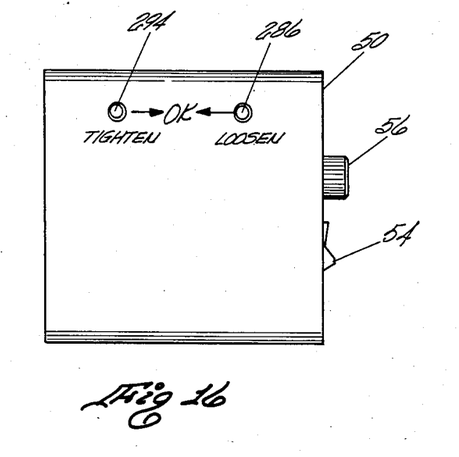
FIG. 16 is a front plan view of the exterior of the monitoring apparatus showing the illumination devices for indicating the tightness of the gastric band.
Figure 17:
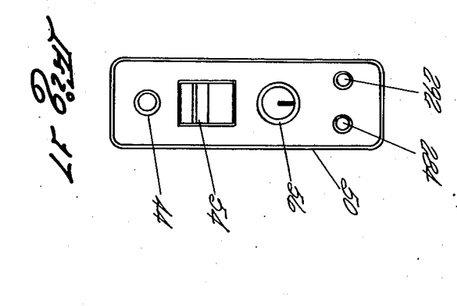
FIG. 17 is a front side view of the monitoring apparatus of FIG. 16.

FIG. 16 and 17 illustrate the monitoring apparatus 40 with the location of the light emitting diodes 282, 284, 292, and 294 located thereon to visually provide the information to the surgeon. The light emitting diodes 294 and 286 are located on the front of the monitoring apparatus and are labeled with appropriate terms "tightened" for light emitting diode 294 and "loosen" for light emitting diode 286. Light emitting diodes 284 and 292 with similar labels are located on the side of the monitoring apparatus 50 as shown in FIG. 17. The sensitivity adjusting means 56 is adjustable from the side of the monitoring device. Also, the on off switch 54 is located in the side panel. The closed fluid channel is passed in the monitoring apparatus through inlet 44 which is located on the front the panel on the monitoring apparatus 50.

Figures 18, 19:
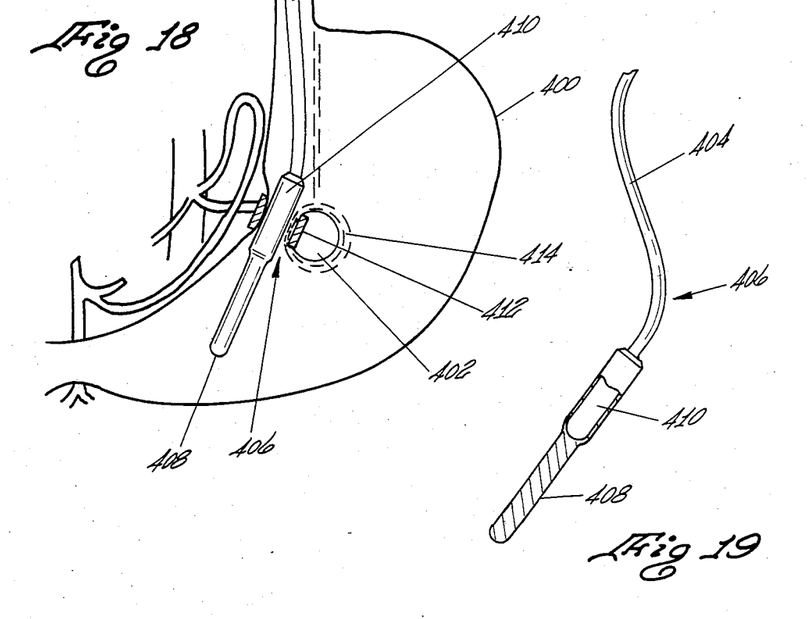
FIG. 18 is a pictorial representation of use of another embodiment of a calibrating apparatus using the teachings of the present invention in the vertical banded gastroplasty operation.
FIG. 19 is a pictorial representation, partially in cross-section showing the sensor and the probe extending from the end thereof.

FIG. 18 illustrates another embodiment of the calibration apparatus which can be utilized for the known vertical banding gastroplasty operation. The calibrating apparatus 406 is inserted into the stomach and proceeds until the probe 408 passes through the space located between the outer wall of the stomach 400 and the location where an incision 402 has been made and staples or sutures 414 have been inserted in place, firmly securing the walls of the stomach together forming a closed opening such that the adjustable gastric band 412 actually passes through an incision 402 and around the periphery of the stomach 400. The probe 408 is attached to sensor 410 which, in turn, is attached to the single-lumen tubing 404. The surgeon feels the location of the probe 408 and inserts an adjustable gastric band through the incision 402 and around the stomach 400. Then the surgeon adjusts the gastric band 412 to apply the appropriate pressure to the sensor 410. The monitoring apparatus will advise the surgeon when the appropriate pressure and predetermined cross-sectional diameter has been obtained.

FIG. 19 illustrates in greater detail the calibrating apparatus 406 comprising the single-lumen tubing 404, the sensor 410 and a probe 408.

Figure 20:
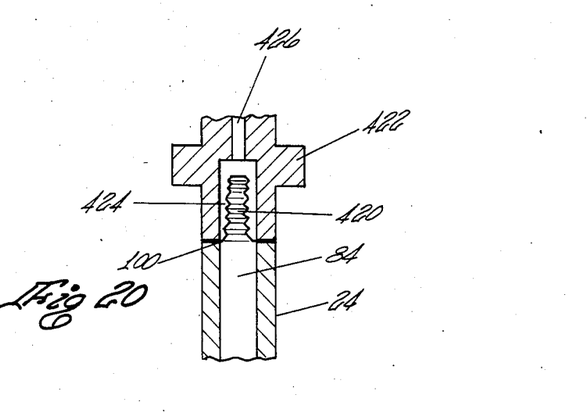
FIG. 20 is a pictorial representation of a transducer which is operatively coupled between the first orifice, at the proximal portion of the single-lumen tubing, and the closed fluid channel.

FIG. 20 illustrates one embodiment of a transducer which may be used to isolate the fluid in the calibrating apparatus from the closed fluid channel in the monitoring system. The transducer is operatively coupled to the first orifice 100 located at the proximal portion of the single-lumen tubing 24. A bellows type member 420 is clamped between a housing member 422 which has a cavity 424 formed therein. The cavity communicates with the closed fluid channel 426. The transducer functions to maintain the fluid within the interior 84 of the single-lumen tubing 24 and the fluid within the cavity 106 separate from the closed fluid channel. The pressure from the calibrating apparatus is transmitted by the bellows member 420 to the fluid in the closed fluid channel 426. As described in connection with FIG. 15, closed fluid channel 426 may be operatively connected to monitoring apparatus through an inlet 44 as illustrated in FIG. 17.

The calibrating apparatus and monitoring system described therein has, as its preferred embodiment, the use of the same in a method for performing a gastric banding operation on the stomach of human body. Also as described hereinabove, the calibrating apparatus can be utilized in connection with known surgical procedures for ensuring that the diameter of the passageway can be set and checked for a predetermined cross-sectional diameter. The calibrating apparatus may be used without the balloon illustrated in FIG. 18.

It is envisioned that the calibrating apparatus and monitoring system disclosed herein can be used in other applications. For example it may be desirable in a mechanical operation to set a flexible tubing at a predetermined cross-sectional diameter and it is readily apparent that the calibration apparatus itself or the calibration apparatus in combination with the monitoring apparatus or the monitoring system itself can be utilized in such applications.

It is further envisioned that the calibration apparatus and the method for using the same and the monitoring system discussed herein can be utilized for precision measurements in the medical field and in non-medical field including scientific or industrial precision measuring applications.

What is claimed is:

1. A method for performing a gastric banding operation on the stomach of a human body comprising the steps of
   inserting into the opening of the stomach of a human body a calibrating apparatus comprising a single-lumen tubing which has a first orifice at the proximal portion thereof and a second orifice at the distal tip thereof which is operatively coupled to an elongated thin-walled sensor having a circular cross-section and which defines a cavity within the interior thereof and wherein the thin-walled sensor is capable of having its cross-sectional diameter varied in response to a variable force being applied to the exterior of the sensor, a toroidal-shaped balloon operatively coupled to and surrounding the exterior of the single-lumen tubing at a preselected location near the distal tip and an elongated tubing which extends from a location exterior to the single-lumen tubing, through the interior of the single-lumen tubing, and into communication with the interior of the balloon and proceeding the calibrating apparatus into the interior of the stomach;
   inflating the balloon while the calibrating apparatus is within the stomach by passing a fluid under pressure through said elongated tubing to expand the balloon to a selected expanded dimension and retrograding the inflated balloon against the stomach opening;
   constricting the stomach located immediately below the expanded balloon by applying a adjustable gastric band around the periphery of the stomach and urging the interior of the stomach into engagement with and around the exterior of the sensor;
   tightening the adjustable band around the periphery of the stomach, which in turn applies pressure around the periphery of the exterior of the sensor, until a selected pressure is detected as being applied to the sensor and suturing the band to form a passageway between the inner walls of the stomach wherein the passageway has a diameter which is substantially equal to the cross-sectional diameter of the sensor at the applied pressure developed by the adjustable band to establish an upper cavity having a volume which is substantially equal to the selected expanded dimension of the balloon and a lower cavity which commuuniates with the first cavity through said passageway having said predetermined cross-sectional area;
   suturing together the sidewalls of the stomach forming the upper and lower cavities enclosing the adjustable gastric band to defining an annular-shaped opening around the adjustable gastric band; and
   withdrawing the fluid from the interior of the balloon, collapsing the same, and retrograding the calibrating apparatus through the opening of the first cavity and out of the human body.

2. The method of claim 1 further comprising the step of
   monitoring the air pressure within the interior of the single-lumen tubing and in the cavity of said sensor with a monitoring means which indicates when the pressure being applied to said sensor by the adjustable gastric band urging the inner walls of the stomach against the sensor is within a predetermined range of forces representing variances in the geometrical dimension of the cross-sectional diameter of the sensor.

3. The method of claim 2 wherein said monitoring means includes means for indicating when the pressure is in excess of a maximum predetermined pressure representing a geometrical dimension of the cross-sectional diameter which is smaller than a predetermined diameter, for indicating when the pressure is less than a minimum predetermined pressure, representing a geometrical dimension of the cross-sectional area which is larger than a predetermined diameter and for indicating when the pressure is at the predetermined pressure wherein the geometrical dimension of the cross-sectional diameter is at said predetermined diameter, and further comprising the step of:
   indicating with a signal means the pressure being monitored by said monitoring means.

4. The method of claim 3 wherein said monitoring means includes a transducer operatively coupled to the single-lumen tubing of said calibrating apparatus at said first orifice which senses a change in pressure of a fluid within the interior of said single-lumen tubing and comprising the step of
   converting the pressure detected by said sensor into a visual light signal on a monitoring apparatus.

5. The method of claim 4 further comprising the steps of
   applying the change of pressure detected by said monitoring apparatus to pressure responsive switching means which selectively energizes light emitting diodes indicating whether the pressure being applied to said sensor is at least one of greater than, less than and equal to a predetermined pressure.

6. The method of claim 3 wherein said predetermined diameter is in a range of about 10 millimeters to about 13 millimeters.

7. The method of claim 1 wherein the selected expanded dimension of the balloon has a volume of about one ounce.

8. The method of claim 1 wherein said adjustable gastric band comprises a dacron reinforced mesh band having a tongue at one end thereof and a fastening member at the other end thereof and wherein said fastening member includes a slot which is adapted to receive and pass the tongue end of the adjustable band, further comprising the step of passing the tongue end of the adjustable band through the slot to the fastening member and tightening the same to the predetermined diameter.

* * * * *